United States Patent [19]

Schindler et al.

[11] Patent Number: 4,784,953

[45] Date of Patent: Nov. 15, 1988

[54] PROCESS AND MICROORGANISM FOR DEGRADING STEROIDS

[75] Inventors: Joachim Schindler, Hilden; Rolf Schmid, Dusseldorf, both of Fed. Rep. of Germany

[73] Assignee: Henkel Kommanditgesellschaft auf Aktien, Duesseldorf, Fed. Rep. of Germany

[21] Appl. No.: 620,537

[22] Filed: Jun. 14, 1984

Related U.S. Application Data

[63] Continuation of Ser. No. 361,685, Mar. 25, 1982, abandoned.

[30] Foreign Application Priority Data

Apr. 1, 1981 [DE] Fed. Rep. of Germany ....... 3113053

[51] Int. Cl.$^4$ ...................... C12P 17/06; C12N 15/00; C12N 1/20; C12R 1/01
[52] U.S. Cl. .................. 435/125; 435/172.1; 435/253; 435/822
[58] Field of Search ............. 435/125, 253, 822, 172.1

[56] References Cited

U.S. PATENT DOCUMENTS 4,042,459  8/1977  Knight et al. ................... 195/51 S
4,097,335  6/1978  Pyke et al. ........................ 435/125
4,176,123  11/1979  Knight et al. .................... 260/345.2
4,304,860  12/1981  Knight et al. ...................... 435/125
4,329,432  5/1982  Knight et al. ...................... 435/253

FOREIGN PATENT DOCUMENTS 2746323  1/1978  Fed. Rep. of Germany.
2387288  4/1978  France.

OTHER PUBLICATIONS

Hashimoto et al., Biochem. J., (1977), 164, 715–726.
T. Nakamatsu et al., Agric. Biol. Chem., 44(7), 1469–1474, (1980).
V. Schömer et al., European J. Appl. Microbiol. Biotechnol., 10, 99–106, (1980).
Freeman, *Textbook of Microbiology*, 22nd Edition, W. B. Saunders Company, Philadelphia, 174–176, (1985).

*Primary Examiner*—Esther M. Kepplinger
*Attorney, Agent, or Firm*—Ernest G. Szoke; Henry E. Millson, Jr.

[57] ABSTRACT

A novel microorganism, mutant chol 149-K14 (DSM 2065) and process for the preparation of 3aα-H-4α-(3'-propionic acid)-5α-hydroxy-7aβ-methyl-hexahydro-1-indanone and the δ-lactone thereof comprising culturing a steroid compound of animal or plant origin with the above microorganism mutant in an aqueous nutrient medium under aerobic conditions.

7 Claims, No Drawings

PROCESS AND MICROORGANISM FOR DEGRADING STEROIDS

This application is a continuation of application Ser. No. 361,685 filed Nov. 25, 1982 now abandoned.

BACKGROUND OF THE INVENTION

It is known in the art that certain microorganisms, particularly certain microorganism mutants, form hexahydroindanone derivatives as intermediate degradation products in the degradation of steroid compounds. For example, it is known that a mutant strain derived from Nocardia corallina IFO 3338 will degrade cholesterol to form 3 aα-H-4α- (3'-propionic acid)-5α-hydroxy-7aβ-methyl-hexahydro-1-indanone-δ-lactone, which has the following structural formula:

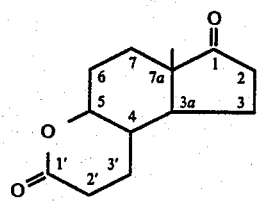

See, e.g. T. Nakamatsu et al., Agric. Biol. Chem., 44(7), 1469-1474 (1980). The primary reaction product formed during the fermentation stage is the free carboxylic acid, 3-(5α-hydroxy-7aβ-methyl-1-oxo-3aα-H-hexahydroindane-4α-yl) propionic acid. When the fermentation broth containing this carboxylic acid is acidified with sulfuric acid to a pH of 2.0 or less, the δ-lactone of Formula I above is formed therefrom. See, e.g., French Pat. No. 2,387,288. Other authors report the conversion of sitosterol with the mutant Nocardia sp.M29 to the above hydroxy carboxylic acid. See V. Schömer et al., European J. Appl. Microbiol. Biotechnol.10, 99-106 (1980). Other disclosures regarding the formation of partial decomposition products of sterols, in particular sitosterol, can be found in the U.S. Pat. Nos. 4,176,123 and 4,042,459, as well as in the Federal Republic of Germany Pat. DE-OS 2,746,323. Even during microbial degradation of bile acids, the formation of hexahydro-1-indanone-δ- lactone could be detected—see Nakamatsu et al, supra, p. 1473, and Hashimoto et al, Biochem. J., 164,715 (1977).

DETAILED DESCRIPTION OF THE INVENTION

It has now been found that when a previously unknown microorganism mutant, K14, which was obtained when a cholesterol-degrading wild strain Chol 149 was treated with UV light, was used for the microbial degradation of naturally occuring steroid compounds of animal and plant origin using an aqueous nutrient under aerobic conditions, 3aα-H-4α- (3'-propionic acid)-5α- hydroxy- 7a-methyl-hexahydro-1-indanone and the δ-lactone thereof were obtained.

The new microorganism mutant Chol 149-K14 was catalogued in the German reference collection of microorganisms (DSM), Griesbach Strasse 8, D/3400, Göttingen; its assigned number is DSM 2065. A subculture of this microorganism will be freely available from this depository upon request upon the granting of a United States Patent wherein the deposited microorganism is part of the disclosure of the invention. It is understood, however, that such availability will not express or imply a right or license to use the organism under any patent. "Mutant Chol. 149-K14 has been identified as a mutant of the microorganism *Rhodococcus erythropolis* of the family Nocardiaceae. The identification was made from physiologic and chemotaxonomic characteristics of the microorganism. Details of the culture media and analytical techniques used for the identification are as follows:

COLONY STRUCTURE AND COLOR

In the case of growth of the microorganism DSM No. 2065 on GC agar (E. Merck, Darmstadt, Federal Republic of Germany), the colonies show a blunt, slightly folded surface; the consistency is firm. No aerial mycelium is formed. The colonies are not strikingly colored. The color shade corresponds to 1014 (ivory) on the RAL color table or ca2 on the Ostwald color table. According to the coding of Seile (1983), the colony form and color is to be assigned the code (11) (pearl white, yellowish).

MICROSCOPY

Young cultures form short, slightly brownish hyphae, which soon break down into cocci-like elements.

| DSM No. | CHEMOTAXONOMY Mycolic Acid Types | | | |
|---|---|---|---|---|
| | Corynemycolic acid | C/N | Nocardomycolic acid | Mycolic acid sensu stricto |
| 2065 | − | + | − | − |

Pyrolysis Products of Mycolic Acid Methyl Ester (MAMES)

When MSME is heated above 280° C., it breaks down into aldehydes and a fatty acid methyl ester (FAMES). The fragments are of taxonomic significance:

| DSM No. | 12:0 | 14:1 | 14:0 | 16:1 | 16:0 | 18:1 | 18.0 | (FAMES in %) |
|---|---|---|---|---|---|---|---|---|
| 2065 | 12 | 2 | 29 | 5 | 45 | 3 | 4 | |

| DSM No. | Percentage Distribution of Fatty Acids from Whole-Cell Hydrolyzates | | | | | | | | | | | | | | | |
|---|---|---|---|---|---|---|---|---|---|---|---|---|---|---|---|---|
| | saturated | | | | | branched iso | | | | | anteiso | | unsaturated | | branched 10 methyl | | |
| 2065 | 14 16 18 | | | 15 17 | | 14 16 18 | | 15 17 | | 15 17 | | 16 18 17 | | 16 18 17 | | |
| | 3 47 1 | | | 1 | | | | | | | | 12 11 | | 25 | | |

| | Percentage Distribution of Menaquinones from Purified Cell Extracts | | | | | | | | | | | | | | |
|---|---|---|---|---|---|---|---|---|---|---|---|---|---|---|---|
| DSM No. | 7/0 | 7/2 | 7/4 | 8/0 | 8/2 | 8/4 | 8/6 | 9/0 | 9/2 | 9/4 | 9/6 | 9/8 | 10/0 | 10/2 | 10/4 | 10/6 |
| 2065 | | | | 1 | 93 | | | tr | 6 | tr | | | | | | |

PHYSIOLOGY

C-source utilization spectrum for differentiation of coryneform organisms with short-chain mycolic acids (C or N), MK-8(H2) and tuberculostearic acid (10-Me).

| DSM No. | N—Val | SuccA | AdipA | CitrA | GlucA | Leu. | Asp. | AspA. | D-Rib | L-Ara |
|---|---|---|---|---|---|---|---|---|---|---|
| 2065 (11) | + | + | + | + | (+) | + | + | + | (+) | − |

| DSM No. | adenine | tyrosine | capryl. | fermentative |
|---|---|---|---|---|
| 2065 | − | + | | − |

Mutant Chol. 149-K14 was prepared from wild strain Chol. 149 as follows: A preparation and treatment of culture of wild strain Chol 149:

The wild strain Chol. 149, which is known available microorganism, was obtained and isolated after testing by the normal screening procedure (ability to grow on cholesterol, tested on a plate). Chol 149 was grown in the following nutrient solution at 30° C. (nutrient medium A): 0.8% peptone, 0.9% yeast extract, 0.3% glucose, 0.06% TWEEN 80 (polyoxyethylene sorbitan monooleate), 0.06% sitosterol, pH 7.2. After the cells of Chol 149 reached the logarithmic growth phase, the cells were centrifuged under sterile conditions washed twice with sterile 0.1M phosphate buffer (pH 6.5) resuspended in the same buffer, and the cell density adjusted under a microscope to 10.8 cells/ml. 8 ml of this cell suspension was placed into a petri dish, and exposed to UV light (distance 30 cm; UV lamp from the E. Schuett Corp. Göttingen, Germany), for twenty seconds. The cell suspension so treated was then resuspended in fresh nutrient solution, and incubated. B. Selection and isolation of Chol 149–K14 using the penicillin and replica transfer method: The culture obtained in (A) above was incubated in a shaking machine for 72 hours at 30° C., until a cell titer of greater than 10.9 cells/ml was reached. 0.1 ml of this incubated cell suspension was transferred into 10 ml of the following nutrient solution (nutrient medium B): 0.05% NaH$_2$PO$_4$, 0.20% K$_2$HPO$_4$, 0.05% MgSO$_4$.7H$_2$O, 0.02% CaCl$_2$.2H$_2$O, 0.005% MnSO$_4$.4H$_2$O, 0.005% (Fe)$_2$SO$_4$.7H$_2$O, 0.10% (NH$_4$)$_2$SO$_4$, 0.0001% biotin, 0.10% TWEEN 80, and 0.10% hexahydro-1-indanone-δ-lactone. After shaking for 18 hours at 30° C., a fresh preheated nutrient solution of the same composition (nutrient medium B) was used to dilute the cell suspension to 10.6 cells/ml. 1000 IU penicillin G was added, and the cell suspension incubated for an additional 7 hours at 30° C. The cells were then centrifuged to remove them from the penicillin antibiotic, washed with a sterile, physiologic sodium chloride solution, and the cells incubated for an additional 3 days, using a nutrient solution of the above composition, except that it contained 0.2% cholesterol in place of hexahydro-1-indanone-δ-lactone. The penicillin G treatment was repeated, and the cell suspension was then transferred onto nutrient medium A plus 1.6% agar. After the cells had multiplied, and visible colonies appeared, the "replica-transfer" technique was used to transfer them onto nutrient medium B plus 1.6% agar. The colonies of mutant Chol 149-K14 were then selected, and isolated. They exhibited little or no growth on nutrient medium B. This new microorganism mutant (referred to hereinafter as "Mutant DSM 2065") exhibits excellent characteristics for use in the partial degradation of naturally occuring steroid compounds, producing the above propionic acid, and from the acid the corresponding-δ-lactone, in good yield.

Steroid starting materials that can be used in the practice of the invention include natural sterols such as cholestrol, sitosterol, stigmasterol and/or ergosterol. Steroid derivatives such as cholestanone, sitostanone, stigmastanone and others can also be employed. In addition, bile acids can be used, such as cholic acid, deoxycholic acid, lithocholic acid, and mixtures thereof. Furthermore, other compounds having a basic steroid structure can be employed, such as the partial degradation products of natural sterols, where the C-17 substituent is either partially or completely degraded.

The process for culturing Mutant DSM 2065 with a steroid compound can be carried out using known techniques and nutrient solutions. One or more of the above steroid compounds are added to the microorganism culture during the incubation period or added to the nutrient medium prior to inoculation with Mutant DSM 2065. The steroids are usually added to the culture in amounts of from 0.1 to 100 g/l, but usually not over 50 g/l. Amounts in the range of from about 1 g/l to about 30 g/l are preferred. The optimum concentration of steroids can readily be determined by simple initial experiments using different concentrations. It is advantageous to add the steroids continuously to the reaction mixture while the degradation reaction is taking place, in order to increase the yields of the desired degradation products.

The culture is grown in a nutrient medium which has as its carbon source either the steroid compounds to be transformed or additional carbon sources that can be metabolized, as well as the usual nutrient and growth substances for these microorganisms. Especially suitable for growing the microorganisms are paraffin, glycerine, carboxylic acids, starches, dextrin, sucrose, glucose, fructose, and sugar-containing waste products. Suitable nitrogen sources are ammonium salts, nitrates, peptone, corn steep liquor, soya flour, distillers vinasse and fish meal. In addition, fermentation accelerators can be added, such as yeast extract and vitamins. In addition, the nutrient mixture usually contains inorganic salts such as sodium-, potassium- or ammonium phosphate, and calcium, magnesium, manganese, and/or iron salts.

Emulsification of the steroid starting material in the nutrient medium is beneficial and is usually achieved by using known emulsifiers such as fatty acid-sorbitan esters or their ethylene-oxide adducts, polyoxyethylene; monolaurylether; or fatty acid amidoalkylbetaine.

The culture medium must be sterilized by heating prior to growing Mutant DSM 2065 therein. After cooling and inoculating the culture medium with a suitable test culture containing Mutant DSM 2065, and incubating at 25°–50° C., preferably at 27°–30° C., the pH value of the nutrient solution is about pH4 to about 8.5, and preferably about 6.8 to about 8.0.

The culture is incubated to the desired stage with shaking, stirring, or gaseous oxygen additions until substantially all of the steroid compound is degraded.

The degradation of the steroid compound usually requires from about 24 to about 160 hours, depending on the substrate concentration and other fermentation conditions. The use of other inhibitors or growth inhibitors for the microorganisms is not needed.

After completion of the fermentation, the cells are usually separated from the nutrient broth, e.g. by filtration, and the product is then separated from the nutrient broth as follows. It was found advantageous to first acidify the nutrient broth to pH 2.0 or less. The nutrient broth is then concentrated in a thin layer evaporator. Mineral acids are suitable for acidifying the broth, but organic acids can also be used; preferred is sulfuric acid.

The concentrated and acidified culture broth is extracted using a solvent that is not freely miscible with water. Suitable solvents are e.g. methyl-isopropyl ketone; an acetic acid ester; hexanol; n-octanol; n-hexane; or a halogenated hydrocarbon compound such as chloroform or methylene chloride. After evaporation of the organic phase, the raw reaction product precipitates, and can be purified by usual procedures, e.g. crystallization. The product obtained is 3aα-H-4α-(3'-propionic acid)-5α-hydroxy-7aβ-methyl-hexahydro-1-indanone-δ-lactone.

The 3aα-H-4α-(3'-propionic acid)-5α-hydroxy-7aβ-methyl-hexahydro-1-indanone-δ-lactone and the corresponding substituted propionic acid derivative (which is present in the broth prior to acidification) which can be obtained by the present process are important intermediates for the manufacture of pharmaceutically active sterol compounds. For example, they are very important for the sythesis of 19-norsteroids, see, e.g. U.S. Pat. No. 4,042,459, column 4 lines 52–63.

The process of the invention is exemplified by the following example which is given for illustration purposes only and not to limit the invention.

EXAMPLE

Mutant DSM 2065 was grown in a 75L fermenter (volume 50L) at 30° C., using the following nutrient medium:

| 0.50 wt % | glucose |
| 0.5 wt % | yeast extract |
| 0.80 wt % | corn steep liquor |
| 1.50 wt % | corn paste |
| 0.13 wt % | $K_2HPO$ |
| 0.09 wt % | $(NH_4)_2 HPO_4$, pH 7.0 |

After a 24-hour incubation period, there was added in sequence:

| 0.1 wt % | cholesterol, and |
| 0.05 wt % | of an emulsifier (DK-ester F50) |

After 6 more hours there was added over a 36-hour period:

| 0.5 wt % | emulsifier (DK-ester F50), plus |
| 1.5 wt % | cholesterol, plus |
| 0.5 wt % | glucose |

After 124 hours of fermentation, the fermentation was discontinued and the cells filtered off. The cell-free culture broth was concentrated 3:1 in a thin layer evaporator, and the concentrate adjusted to pH 0.2 with aqueous sulfuric acid, and finally extracted with methylene chloride in a 1:1 volume ratio. The methylene chloride phase was then separated. After evaporating the organic phase, there was obtained 3aα-H-4α-(3'-propronic acid) -5α-hydroxy-7aβ-methylhexahydro-1-indanone-δ-lactone in a yield of about 63 mole %.

What is claimed is:

1. A process for the preparation of 3aα-H-4α-(3'-propionic acid)-5α-hydroxy-7aβ-methyl-hexahydro-1-indanone and the δ-lactone thereof comprising culturing a steroid compound of animal or plant origin with a microorganism mutant Chol 149-K14 (DSM 2065) in an aqueous nutrient medium under aerobic conditions to degrade the steroid compound to said indanone, and recovering said indanone and the δ-lactone derivative thereof.

2. A process in accordance with claim 1 wherein the steroid compound of animal or plant origin is at least one selected from the group consisting of cholesterol, sitosterol, stigmasterol, ergosterol, cholestanone, sitostanone, stigmastanone, and a bile acid.

3. A process in accordance with claim 1 or 2 wherein the steroid compound is present in a concentration ranging from about 0.1 to about 100 g/l.

4. A process in accordance with claim 1 or 2 wherein the aqueous nutrient medium is maintained at a temperature in the range of from about 25° to about 50° C.

5. A process in accordance with claim 1 or 2 wherein the pH of the aqueous nutrient medium is in the range of from about 4 to about 8.5.

6. A process in accordance with claim 1 wherein following culturing of the microorganism, the microorganism cells are separated from the nutrient medium, the nutrient medium is acidified to a pH of about 2.0 or less, concentrated, extracted with a solvent not freely miscible with water to extract the desired product, and the solvent removed from said product.

7. A biologically pure culture of the microorganism mutant Chol 149-K14 (DSM 2065).

* * * * *